United States Patent
Taylor

(10) Patent No.: US 9,612,216 B2
(45) Date of Patent: Apr. 4, 2017

(54) BAG SEAL INSPECTION DEVICE

(75) Inventor: Alfred Alexander Taylor, Lugarno (AU)

(73) Assignee: TNA Australia Pty Limited, Lidcombe (AU)

(*) Notice: Subject to any disclaimer, the term of this patent is extended or adjusted under 35 U.S.C. 154(b) by 572 days.

(21) Appl. No.: 13/506,185

(22) Filed: Apr. 2, 2012

(65) Prior Publication Data

US 2012/0255260 A1    Oct. 11, 2012

(30) Foreign Application Priority Data

Apr. 11, 2011    (AU) ................................ 2011901363

(51) Int. Cl.
*B29C 65/18*    (2006.01)
*B65B 51/00*    (2006.01)
(Continued)

(52) U.S. Cl.
CPC ............ *G01N 25/72* (2013.01); *B29C 65/18* (2013.01); *B29C 66/1122* (2013.01); *B29C 66/4322* (2013.01); *B29C 66/49* (2013.01); *B29C 66/8161* (2013.01); *B29C 66/8242* (2013.01); *B29C 66/8322* (2013.01); *B29C 66/849* (2013.01); *B29C 66/872* (2013.01); *B29C 66/91216* (2013.01); *B29C 66/91221* (2013.01); *B29C 66/91411* (2013.01); *B29C 66/91431* (2013.01); *B29C 66/961* (2013.01); *B65B 9/2028* (2013.01); *B65B 51/26* (2013.01); *B65B 57/00* (2013.01); *G01M 3/002* (2013.01); *G01M 3/38* (2013.01); *B31B 2201/95* (2013.01); *B31B 2219/95* (2013.01)

(58) Field of Classification Search
CPC ..... B29C 65/18; B29C 66/49; B29C 66/8322; B29C 66/91411; B29C 66/961; G01N 25/72; B65B 51/14; B65B 51/14; B65B 51/146; B65B 51/26; B65B 2051/105; B65B 2220/08
USPC .... 156/358, 359, 361, 367, 378, 379, 583.1; 493/133, 135, 189, 207; 53/167
See application file for complete search history.

(56) References Cited

U.S. PATENT DOCUMENTS 2,899,875 A * 8/1959 Leasure ............... B29C 65/7847
493/302
3,618,740 A * 11/1971 Taverna ...................... 198/343.1
(Continued)

FOREIGN PATENT DOCUMENTS

EP        0616942 A1    9/1994
EP    1 186 876 A2    3/2002
(Continued)

OTHER PUBLICATIONS

Examination and Search Report for Great Britain Application No. GB1206303.8, 4 pages.
(Continued)

*Primary Examiner* — George Koch
(74) *Attorney, Agent, or Firm* — Kilpatrick Townsend & Stockton LLP

(57) ABSTRACT

A device to inspect a longitudinal heat seal in tubular bag material. The seal is formed by a heated sealing bar (14). Downstream of the bar (14) is a heat sensing camera (20) that sends a signal to a central processing unit (21). The unit (21) will then identify any faults in the seal.

10 Claims, 1 Drawing Sheet

(51) Int. Cl.

| | |
|---|---|
| *G01N 25/72* | (2006.01) |
| *G01M 3/00* | (2006.01) |
| *G01M 3/38* | (2006.01) |
| *B29C 65/00* | (2006.01) |
| *B65B 51/26* | (2006.01) |
| *B65B 57/00* | (2006.01) |
| *B65B 9/20* | (2012.01) |

(56) References Cited

U.S. PATENT DOCUMENTS

| | | | |
|---|---|---|---|
| 3,925,139 | A | 12/1975 | Simmons |
| 4,663,917 | A | 5/1987 | Taylor et al. |
| 4,910,943 | A | 3/1990 | Taylor et al. |
| 6,041,646 | A | 3/2000 | Fenlon |
| 6,170,227 | B1 * | 1/2001 | Kovacs ................ B31D 5/0078 53/375.9 |
| 6,202,476 | B1 | 3/2001 | Fenlon |
| 6,568,247 | B2 | 5/2003 | Taylor |
| 7,124,559 | B2 | 10/2006 | Taylor |
| 7,415,809 | B2 | 8/2008 | Taylor |
| 7,472,528 | B2 | 1/2009 | Taylor |
| 2002/0033006 | A1 * | 3/2002 | Fukuda ................ B29C 53/50 53/551 |
| 2004/0238529 | A1 | 12/2004 | Keller |
| 2005/0286606 | A1 * | 12/2005 | Ignatowicz ....................... 374/4 |
| 2006/0039444 | A1 | 2/2006 | Brun |
| 2008/0022632 | A1 * | 1/2008 | Gysi et al. .................. 53/377.7 |

FOREIGN PATENT DOCUMENTS

| | | | |
|---|---|---|---|
| EP | 1623930 | A1 | 2/2006 |
| EP | 1947440 | A2 | 7/2008 |
| JP | H09-30514 | A | 2/1997 |
| JP | 2000-227407 | A | 8/2000 |
| JP | 2003-034303 | A | 2/2003 |
| JP | 2003-291911 | A | 10/2003 |
| JP | 2005-502508 | A | 1/2005 |
| JP | 2007-040745 | A | 2/2007 |
| WO | 03/104099 | A1 | 12/2003 |

OTHER PUBLICATIONS

Search Report mailed Apr. 25, 2013 in Spanish Patent Application No. ES201230533, 6 pages.

JP Patent Application No. 2012-088949, Office Action mailed Apr. 4, 2016, 6 pages.

* cited by examiner

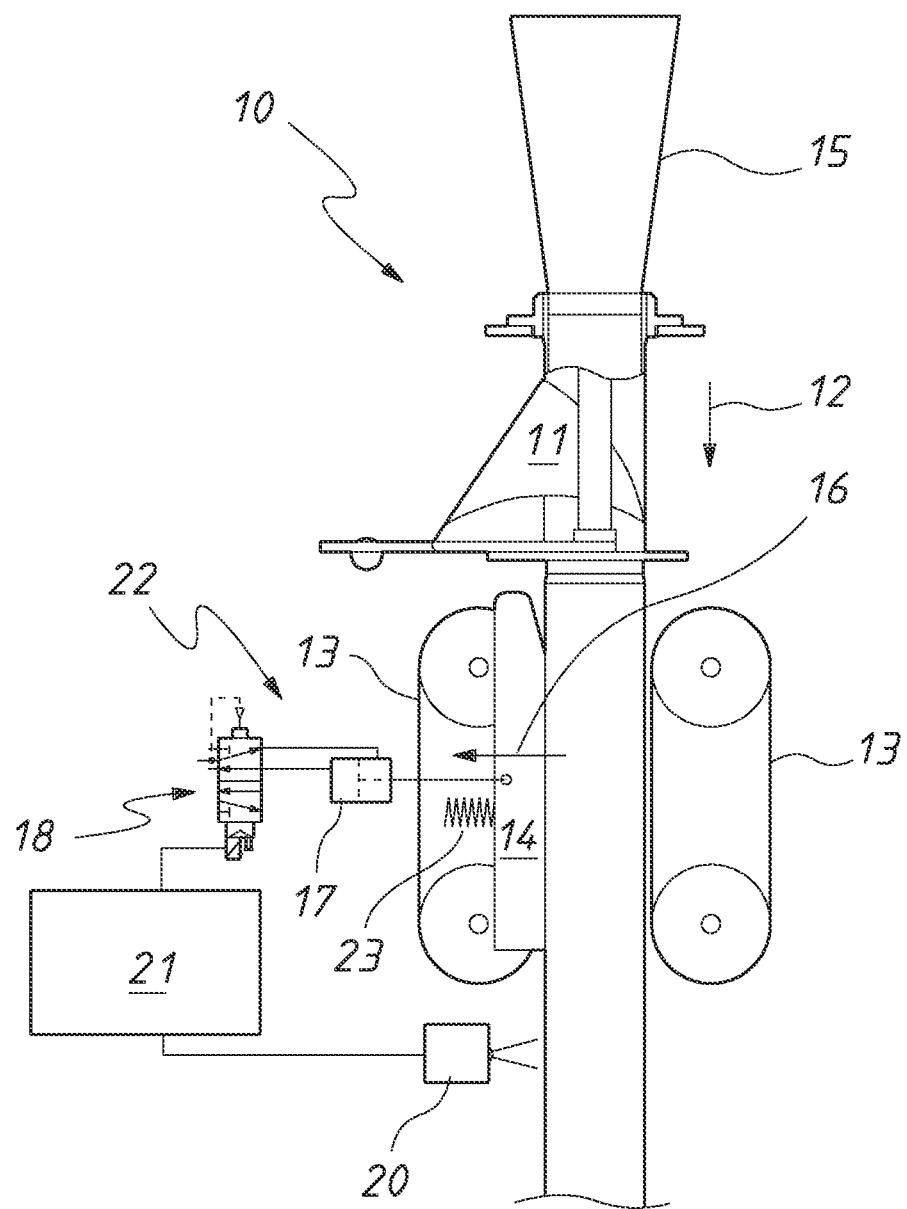

BAG SEAL INSPECTION DEVICE

This application claims priority to Australian Application No. 2011901363, filed Apr. 11, 2011, the disclosure of which is incorporated by reference herein.

TECHNICAL FIELD

The present invention relates to packaging machines that form bags of product, the bags being formed from tubular bag material that is longitudinally sealed and transversely cut and sealed to form the bags.

BACKGROUND OF THE INVENTION

Described in U.S. Pat. No. 4,663,917 is a packaging machine. The packaging machine receives tubular bag material to the interior of which product is delivered. The tubular bag material is formed from a web (strip) that via a former is transformed into the tubular configuration. The longitudinally extending edge portions of the web are joined so as to form a longitudinal seal. Product is delivered to the interior of the tubular bag material, with the packaging machine then transversely sealing are of cutting the tubular bag material, at longitudinally spaced locations, to form bags.

If the longitudinal and/or transverse seals are not properly formed, the product can degrade. Various means have been proposed for checking the integrity of the seals. As an example, seal testing devices are described in U.S. Pat. Nos. 6,568,247, 6,202,476 and 6,041,646.

Previous methods of detecting improperly formed seals have a number of disadvantages including not successful detecting faulty seals, and being unduly complex and unreliable.

OBJECT OF THE INVENTION

It is the object of the present invention to overcome or substantially ameliorate at least one of the above disadvantages.

SUMMARY OF THE INVENTION

There is disclosed herein a device to inspect a longitudinal heat seal in tubular bag material, the bag material being formed of plastics material having longitudinally extending and overlapping edge portions secured together by the heat seal, the device including:

a drive assembly to engage the tubular bag material to move the tubular bag material along a predetermined path in a predetermined direction;

a heat sealing mechanism to engage the longitudinally extending edge portions to heat the edge portions to form said longitudinally extending heat seal; and a camera directed at the heat seal and to provide a signal indicative of the temperature of the heat seal exposed to the camera.

Preferably, said camera provides a signal indicative of infrared radiation emanating from the seal to thereby provide a signal indicative of the temperature of the seal exposed to the camera.

Preferably, the camera provides a signal indicative of any temperature gradient transversely across the seal.

There is further disclosed herein, in combination, the above device, and a heat sealing bar to engage the tubular bag material to form the seal, the bar being supported for movement between an engaging position to engage the bag material to form the seal, and a retracted position, spaced from the engaged position so as not to be engaged with the tubular bag material, and a drive assembly operatively associated with the bar to move the bar between the engaged and retracted positions, the drive assembly also generating a signal delivered to a central process unit to provide an indication of when the bar is engaged with the tubular bag material, with the camera also delivering the camera signal to the unit.

Preferably, the drive assembly includes a spring urging the bar to the engaged position, and a cylinder to move the bar from the engaged position to the retracted position.

BRIEF DESCRIPTION OF THE DRAWINGS

The preferred form of the present invention will now be described by way of example with reference to the accompanying drawing that schematically depicts in sectioned side elevation a device to inspect a longitudinally extending heat seal in tubular bag material to detect faults in the seal.

DETAILED DESCRIPTION OF THE PREFERRED EMBODIMENT

In the accompanying drawing there is schematically depicted a former 10 to which a web of packaging film is delivered. The web is in the form of a strip that engages the former surface 11 so as to be configured into a tubular configuration. Formers are and described in U.S. Pat. Nos. 7,124,559 and 7,415,809. The tubular bag material is driven in the direction 12 engaged with vacuum drive belts 13. The suitable vacuum belt assemblies are described in U.S. Pat. Nos. 4,910,943 and 7,472,528.

The packaging film has longitudinally extending edge portions that overlap when the bag material is in the tubular configuration. The overlapping longitudinally extending edge portions are engaged by a heated sealing bar 14. The heating bar 14 is electrically heated and heats the tubular bag material to cause the plastics material thereof to melt, bond and form a longitudinal seal.

Above the former 11 is a product delivery chute 15 to which batches of product are delivered so as to be located within the tubular bag material. A packaging machine downstream of the belts 13 strips the bag material, forms transverse seals and cuts individual bags of product from the tubular bag material. A suitable packaging machine is described in U.S. Pat. No. 4,663,917.

The bar 14 is mounted on a supporting frame for linear movement in the direction 16, that is a direction transverse of the direction 12, and a direction transverse relative to the tubular bag material and longitudinal seal. The bar 14 is movable between a position of engagement with the tubular bag material to form the seal, and a retracted position spaced from the tubular bag material.

A bar drive assembly 22 moves the bar 14 in the direction 16 and includes pneumatic or hydraulic cylinder 17 is attached to the bar 14, and a valve 18. Preferably, the cylinder 17 is pneumatically operated and receives air under pressure from the valve 18.

The bar 14 is urged to the engaged position by means of a spring 23. Actuation of the cylinder 17 by the valve 18 moves the bar 14 in the direction 16 to move the bar 14 to the retracted position.

Downstream of the bar 14 in the direction 12 is a heat sensing camera 20. The camera 20 is provided to generate a signal indicative of the temperature of the longitudinal seal in the tubular bag material. If there is a fault in the seal, then the area of the fault will be at a lower temperatus. As a particular example, the camera 20 could detect infrared radiation coming from the seal in order to provide a signal indicative of the temperature of the seal. Preferably the camera 20 is also adapted to provide a signal indicative of the temperature gradient across the seal. If the temperature gradient across the seal is not consistent, then again this is indicative of a flaw in the seal.

The camera 20 sends a signal to a central processing unit 21. The processing unit 21 is operatively associated with the packaging machine below, as well as other apparatus such as the drive mechanism for the belts 13, to cease operations should a faulty seal be detected. In particular, the unit 21 could cease operation of the packaging machine and associated apparatus if the temperature of a portion of the seal is outside of the desired range, or the temperature gradient across the seal is not consistent. The unit 21 also controls the valve 18 and therefore is aware of the position of the bar 14 and therefore will not expect a desired temperature of the seal to be detected when the bar 14 is in the retracted position.

The invention claimed is:

1. A device to inspect a longitudinal heat seal in tubular bag material, the bag material being formed of plastics material having longitudinally extending and overlapping edge portions secured together by the heat seal, the device comprising:
   a bag material drive assembly to engage the tubular bag material to move the tubular bag material along a predetermined path in a predetermined direction;
   a heat sealing mechanism to engage the longitudinally extending edge portions to heat the edge portions to form said longitudinally extending heat seal, the heat sealing mechanism comprising a heat sealing bar to engage the tubular bag material to form the seal, the bar being supported for movement between an engaging position to engage the bag material to form the seal, and a retracted position at which the heat sealing bar is removed from contact with the tubular bag material, spaced from the engaged position so as not to be engaged with the tubular bag material, and a bar drive assembly operatively associated with the bar to move the bar between the engaged and retracted positions;
   a camera directed at the heat seal and to provide a signal indicative of the temperature of the heat seal exposed to the camera; and
   a central processing unit to control the bar drive assembly, wherein the signal is delivered from the camera to the central processing unit so that the central processing unit can control the bar drive assembly based on the temperature of the heat seal.

2. The device of claim 1, wherein said camera provides a signal indicative of infrared radiation emanating from the seal to thereby provide a signal indicative of the temperature of the seal exposed to the camera.

3. The device of claim 1, wherein the camera provides a signal indicative of any temperature gradient transversely across the seal.

4. The device of claim 1, wherein the bar drive assembly also generates a signal delivered to the central processing unit to provide an indication of when the bar is engaged with the tubular bag material.

5. The combination of claim 1, wherein the bar drive assembly includes a spring urging the bar to the engaged position, and a cylinder to move the bar from the engaged position to the retracted position.

6. The device of claim 2, wherein the camera provides a signal indicative of any temperature gradient transversely across the seal.

7. The device of claim 2, wherein the bar drive assembly also generates a signal delivered to the central processing unit to provide an indication of when the bar is engaged with the tubular bag material.

8. The combination of claim 7, wherein the bar drive assembly includes a spring urging the bar to the engaged position, and a cylinder to move the bar from the engaged position to the retracted position.

9. The device of claim 3, wherein the bar drive assembly also generates a signal delivered to the central processing unit to provide an indication of when the bar is engaged with the tubular bag material.

10. The device of claim 9, wherein the bar drive assembly includes a spring urging the bar to the engaged position, and a cylinder to move the bar from the engaged position to the retracted position.

* * * * *